(12) United States Patent
Spinelli et al.

(10) Patent No.: US 7,664,549 B2
(45) Date of Patent: *Feb. 16, 2010

(54) CARDIAC RHYTHM MANAGEMENT SYSTEM WITH ARRHYTHMIA CLASSIFICATION AND ELECTRODE SELECTION

(75) Inventors: Julio C. Spinelli, Shoreview, MN (US); Qingsheng Zhu, Little Canada, MN (US); Jeffrey E. Stahmann, Ramsey, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 556 days.

This patent is subject to a terminal disclaimer.

(21) Appl. No.: 11/125,501

(22) Filed: May 10, 2005

(65) Prior Publication Data
US 2005/0203581 A1      Sep. 15, 2005

Related U.S. Application Data

(63) Continuation of application No. 10/027,800, filed on Dec. 20, 2001, now Pat. No. 6,909,916.

(51) Int. Cl.
*A61N 1/362* (2006.01)
(52) U.S. Cl. ..................................... 607/14
(58) Field of Classification Search ............ 607/14
See application file for complete search history.

(56) References Cited

U.S. PATENT DOCUMENTS

| | | | |
|---|---|---|---|
| 4,023,564 A | | 5/1977 | Valiquette et al. |
| 4,390,021 A | * | 6/1983 | Spurrell et al. .............. 607/14 |
| 4,790,317 A | * | 12/1988 | Davies ........................ 607/4 |
| 4,830,006 A | * | 5/1989 | Haluska et al. ............... 607/4 |
| 4,872,459 A | * | 10/1989 | Pless et al. .................. 607/15 |
| 4,880,005 A | | 11/1989 | Pless et al. |
| 5,002,052 A | | 3/1991 | Haluska |
| 5,107,850 A | | 4/1992 | Olive |
| 5,144,947 A | | 9/1992 | Wilson |
| 5,158,092 A | | 10/1992 | Glace |

(Continued)

FOREIGN PATENT DOCUMENTS

EP    0450943 A2    10/1991

(Continued)

OTHER PUBLICATIONS

"European Patent Application No. 02790155.2, Communication mailed May 8, 2007", 2 pgs.

(Continued)

*Primary Examiner*—Kennedy J Schaetzle
(74) *Attorney, Agent, or Firm*—Schwegman, Lundberg & Woessner, P.A.

(57) ABSTRACT

A system, method, or device classifies an arrhythmia according to the temporal order in which a depolarization wave associated with a particular heart contraction is received at a plurality of electrodes. One or more antiarrhythmia therapies is mapped to each arrhythmia classification. When a particularly classified arrhythmia is detected, the correspondingly mapped therapy list is selected and an appropriate antiarrhythmia therapy delivered. In one example, the particular therapy delivered in response to an arrhythmia depends at least in part on its historical success in treating arrhythmias of that classification.

28 Claims, 6 Drawing Sheets

U.S. PATENT DOCUMENTS

| | | | |
|---|---|---|---|
| 5,161,527 A | 11/1992 | Nappholz et al. | |
| 5,161,529 A | 11/1992 | Stotts et al. | |
| 5,181,511 A | 1/1993 | Nickolls et al. | |
| 5,209,229 A | 5/1993 | Gilli | |
| 5,222,493 A | 6/1993 | Sholder | |
| 5,224,475 A | 7/1993 | Berg et al. | |
| 5,251,624 A | 10/1993 | Bocek et al. | |
| 5,257,621 A | 11/1993 | Bardy et al. | |
| 5,324,310 A | 6/1994 | Greeninger et al. | |
| 5,330,505 A | 7/1994 | Cohen | |
| 5,330,508 A | 7/1994 | Gunderson | |
| 5,342,402 A | 8/1994 | Olson et al. | |
| 5,350,410 A | 9/1994 | Kleks et al. | |
| 5,379,776 A | 1/1995 | Murphy et al. | |
| 5,425,749 A | 6/1995 | Adams | |
| 5,431,689 A * | 7/1995 | Weinberg et al. | 607/14 |
| 5,447,519 A | 9/1995 | Peterson | |
| 5,458,620 A | 10/1995 | Adams et al. | |
| 5,472,453 A | 12/1995 | Alt | |
| 5,548,619 A | 8/1996 | Horiike et al. | |
| 5,587,970 A | 12/1996 | Greenwood | |
| 5,587,977 A | 12/1996 | Murata | |
| 5,591,215 A * | 1/1997 | Greenhut et al. | 607/14 |
| 5,662,688 A | 9/1997 | Haefner et al. | |
| 5,683,424 A | 11/1997 | Brown et al. | |
| 5,683,431 A | 11/1997 | Wang | |
| 5,755,736 A * | 5/1998 | Gillberg et al. | 607/4 |
| 5,755,737 A | 5/1998 | Prieve et al. | |
| 5,779,645 A | 7/1998 | Olson et al. | |
| 5,836,971 A | 11/1998 | Starkweather | |
| 5,846,263 A | 12/1998 | Peterson et al. | |
| 5,855,593 A | 1/1999 | Olson et al. | |
| 5,871,512 A | 2/1999 | Hemming et al. | |
| 5,978,707 A | 11/1999 | Krig et al. | |
| 5,999,854 A | 12/1999 | Deno et al. | |
| 6,076,014 A | 6/2000 | Alt | |
| 6,101,414 A | 8/2000 | Kroll | |
| 6,128,529 A | 10/2000 | Elser | |
| 6,137,308 A | 10/2000 | Nayak | |
| 6,151,524 A | 11/2000 | Krig et al. | |
| 6,167,308 A | 12/2000 | DeGroot | |
| 6,192,275 B1 | 2/2001 | Zhu et al. | |
| 6,221,011 B1 | 4/2001 | Bardy | |
| 6,230,055 B1 | 5/2001 | Sun et al. | |
| 6,266,554 B1 | 7/2001 | Hsu et al. | |
| 6,270,457 B1 | 8/2001 | Bardy | |
| 6,277,072 B1 | 8/2001 | Bardy | |
| 6,280,380 B1 | 8/2001 | Bardy | |
| 6,289,248 B1 | 9/2001 | Conley et al. | |
| 6,312,378 B1 | 11/2001 | Bardy | |
| 6,336,903 B1 | 1/2002 | Bardy | |
| 6,358,203 B2 | 3/2002 | Bardy | |
| 6,368,284 B1 | 4/2002 | Bardy | |
| 6,393,316 B1 | 5/2002 | Gillberg et al. | |
| 6,398,728 B1 | 6/2002 | Bardy | |
| 6,400,986 B1 * | 6/2002 | Sun et al. | 607/14 |
| 6,440,066 B1 | 8/2002 | Bardy | |
| 6,445,949 B1 | 9/2002 | Kroll | |
| 6,449,503 B1 | 9/2002 | Hsu | |
| 6,477,422 B1 | 11/2002 | Splett | |
| 6,480,734 B1 | 11/2002 | Zhang et al. | |
| 6,654,639 B1 | 11/2003 | Lu | |
| 6,671,548 B1 * | 12/2003 | Mouchawar et al. | 607/14 |
| 6,708,058 B2 | 3/2004 | Kim et al. | |
| 6,885,890 B2 | 4/2005 | Spinelli et al. | |
| 6,909,916 B2 * | 6/2005 | Spinelli et al. | 607/9 |
| 6,950,696 B2 * | 9/2005 | Bjorling et al. | 600/515 |
| 2003/0120315 A1 | 6/2003 | Spinelli et al. | |
| 2003/0120316 A1 | 6/2003 | Spinelli et al. | |
| 2003/0191403 A1 | 10/2003 | Zhou et al. | |
| 2004/0167579 A1 | 8/2004 | Sharma et al. | |
| 2004/0215270 A1 | 10/2004 | Ritscher et al. | |
| 2006/0052830 A1 | 3/2006 | Spinelli et al. | |

FOREIGN PATENT DOCUMENTS

| | | |
|---|---|---|
| EP | 0709112 | 5/1996 |
| EP | 1267993 B1 | 1/2005 |
| WO | WO-98/40122 | 9/1998 |

OTHER PUBLICATIONS

"European Patent Application No. 02790155.2, Response filed Nov. 8, 2007 to Communication mailed May 8, 2007", 3 pgs.

"European Patent Application No. 02794339.8, Communication mailed Oct. 27, 2006", 10 pgs.

"European Patent Application No. 02794339.8, Response filed Feb. 27, 2007 to Communication mailed Oct. 27, 2006", 13 pgs.

"PCT Application No. PCT/US02/40907, International Search Report mailed Jul. 18, 2003", 4 pgs.

"PCT Application No. PCT/US02/40909, International Search Report mailed Sep. 18, 2003", 3 pgs.

"Prosecution File History for U.S. Appl. No. 10/027,794", (issued as US 6,885,890), 18 pgs.

"Prosecution File History for U.S. Appl. No. 10/027,800", (issued as US 6,609,916), 43 pgs.

Kerr, M., "Shock Rate Cut 70% with ICDs Programmed to First Deliver Antitachycardia Pacing: Results of the PainFREE Rx II Trial", *NewsRhythms, MedScape CRM News*, www.medscape.com, (© 2003 Medscape), 2 pgs.

Wathen, Mark S., et al., "Shock Reduction Using Antitachycardia Pacing for Spontaneous Rapid Ventricular Tachycardia in Patients With Coronary Artery Disease", *Circulation*, 104(7), (Aug. 14, 2001), 796-801.

Mercando, et al., "Measurement of Differences in Timing and Sequence Between Two Ventricular Electrodes as a Means of Tachycardia Differentiation", *PACE*, Part II, vol. 9, (Nov.-Dec. 1986),1069-1078.

U.S. Appl. No. 10/027,800, filed Dec. 20, 2001, Cardiac Rhythm Management System With Arrhythmia Classification and Electrode Selection System.

\* cited by examiner

CARDIAC RHYTHM MANAGEMENT SYSTEM WITH ARRHYTHMIA CLASSIFICATION AND ELECTRODE SELECTION

CROSS-REFERENCE TO RELATED APPLICATION(S)

This application is a continuation of U.S. patent application Ser. No. 10/027,800, filed on Dec. 20, 2001, now U.S. Pat. No. 6,909,916, the specification of which is incorporated by reference herein.

TECHNICAL FIELD

This document relates generally to cardiac rhythm management systems, devices, and/or methods, and particularly, but not by way of limitation, to a cardiac rhythm management system, device, and/or method that classifies an arrhythmia and selects electrodes for delivering antiarrhythmia therapy using the classification.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poorly spatially-coordinated heart contractions. In either case, diminished blood circulation may result. For such patients, a cardiac rhythm management system may be used to improve the rhythm and/or spatial coordination of heart contractions. Such systems are often implanted in the patient and deliver therapy to the heart. Cardiac rhythm management systems include, among other things, pacemakers, also referred to as pacers. Pacers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency. Cardiac rhythm management systems also include cardiac resynchronization therapy (CRT) devices for coordinating the spatial nature of heart depolarizations for improving pumping efficiency. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together.

Cardiac rhythm management systems also include defibrillators that are capable of delivering higher energy electrical stimuli to the heart. Such defibrillators include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac rhythm management systems also include devices that combine these functions, as well as monitors, drug delivery devices, and any other implantable or external systems or devices for diagnosing or treating the heart.

One problem faced by cardiac rhythm management devices is in determining what type of antitachyarrhythmia therapy to deliver to a patient to interrupt a tachyarrhythmia. For example, antitachyarrhythmia pacing therapy (ATP) is typically preferred to delivering a countershock, since ATP is less painful to the patient. However, in some circumstances, ATP may also be less effective than delivering a shock. Also, the present inventors have recognized that where a plurality of electrodes are associated with the region of the heart to receive antitachyarrhythmia treatment, delivering antitachyarrhythmia therapy from certain electrode(s) may be more effective than delivering the therapy from other electrode(s). The present inventors have also recognized that the efficacy of a particular therapy regimen and/or the selection of particular electrode(s) to provide the therapy may depend on the nature of the arrhythmia itself. For these reasons, the present inventors have recognized a need for classifying an arrhythmia and using the classification to guide the choice and/or nature of the antitachyarrhythmia therapy and/or its delivery.

SUMMARY

This document discusses, among other things, a system, method, or device that classifies an arrhythmia according to the temporal order in which a depolarization wave associated with a particular heart contraction is received at a plurality of electrodes. One or more antiarrhythmia therapies is mapped to each arrhythmia classification. When a particularly classified arrhythmia is detected, the correspondingly mapped therapy list is selected and an appropriate antiarrhythmia therapy delivered. In one example, the particular therapy delivered in response to an arrhythmia depends at least in part on its historical success in treating arrhythmias of that classification.

In one example, this document discusses a cardiac rhythm management system. The cardiac rhythm management system includes a plurality of electrodes associated with a heart. A cardiac signal detector circuit is coupled to the electrodes. An energy output circuit is also coupled to at least one of the electrodes. A controller is coupled to the cardiac signal detector and the energy output circuit. The controller includes an arrhythmia detector module. The controller also includes an arrhythmia classifier module, to classify the detected arrhythmia according to a sequence in which a heart contraction depolarization is received at the electrodes. The controller further includes a therapy map, providing an antiarrhythmia therapy corresponding to the arrhythmia classification. The controller issues a control signal to the energy output circuit to deliver a selected antiarrhythmia therapy corresponding to an arrhythmia classification.

In another example, this document also discusses a method. The method includes detecting an arrhythmia at a plurality of electrodes, classifying the detected arrhythmia according to a sequence in which a heart contraction depolarization is received at the electrodes, selecting an antiarrhythmia therapy corresponding to the arrhythmia classification, and delivering the selected antiarrhythmia therapy by issuing a control signal to the energy output circuit. Other aspects of the invention will be apparent on reading the following detailed description of the invention and viewing the drawings that form a part thereof.

BRIEF DESCRIPTION OF THE DRAWINGS

In the drawings, which are offered by way of example, and not by way of limitation, and which are not necessarily drawn to scale, like numerals describe substantially similar components throughout the several views. Like numerals having different letter suffixes represent different instances of substantially similar components.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. The following detailed description is, therefore, not to be taken in a limiting sense, and the scope of the present invention is defined by the appended claims and their equivalents.

Figure 1:
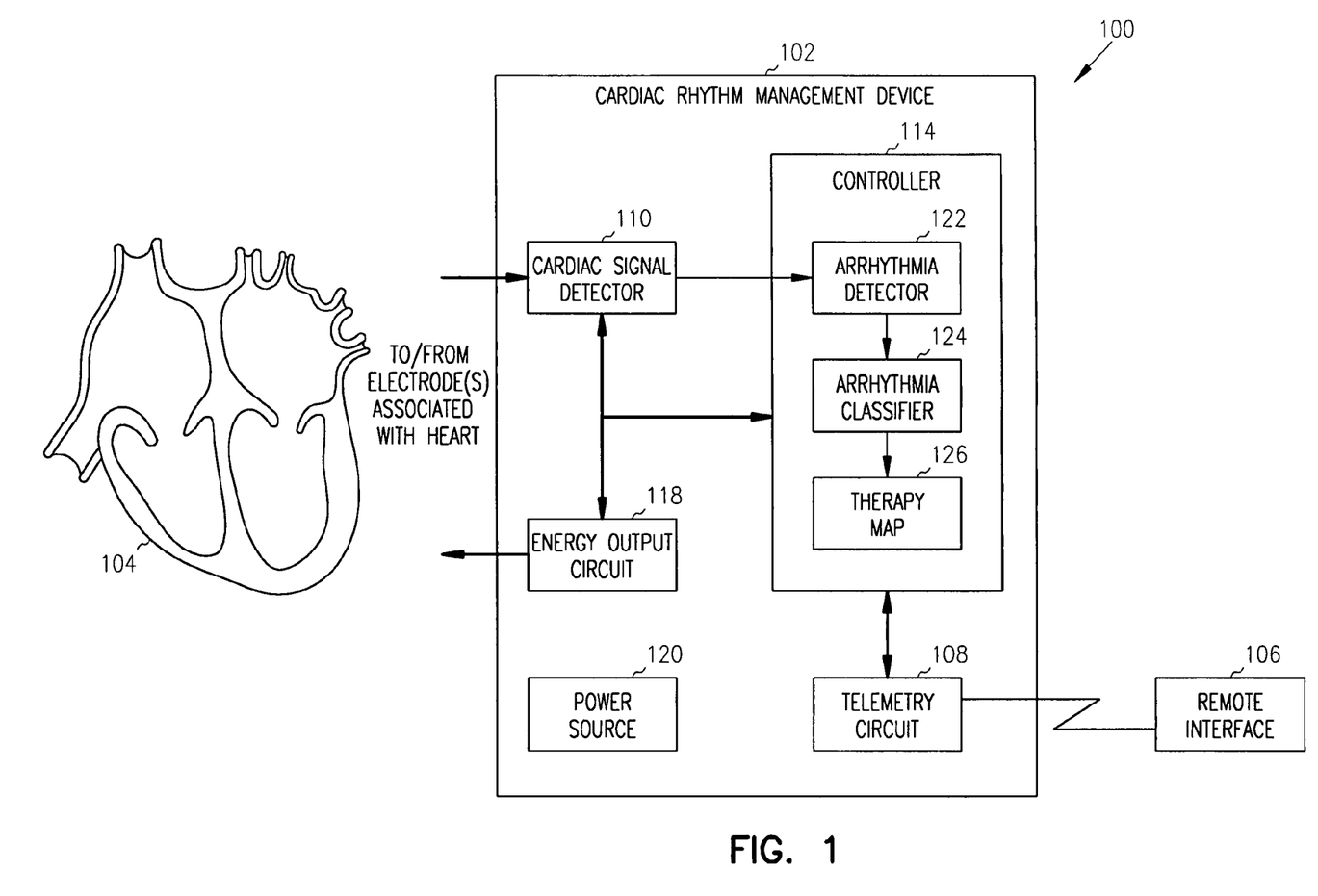
FIG. 1 is a block diagram illustrating generally portions of a cardiac rhythm management system and portions of an environment in which it is used.

FIG. 1 is a block diagram illustrating generally portions of a cardiac rhythm management system 100 and portions of an environment in which it is used. In this example, system 100 includes a cardiac rhythm management device 102 coupled to a heart 104 by one or more electrodes associated with heart 104, such as for sensing intrinsic cardiac signals and/or for delivering energy or other therapy to heart 104. System 100 may also include a programmer or other remote interface 106, which is wirelessly or otherwise communicatively coupled to a telemetry circuit 108 or other communication circuit in device 102. Device 102 includes a pacer, a defibrillator, a cardiac resynchronization therapy (CRT) device, a monitor, a device that combines more than one of these functions, or any other implantable or external device for diagnosing and/or treating the heart.

In one example, device 102 is sized and shaped for being pectorally or abdominally implanted in a human patient. The electrode(s) coupling device 102 to heart 104 may include an intravascular electrode, an intracardiac electrode, an epicardial electrode, or a housing or a header electrode located on a housing of device 102 or a header attached thereto, or any combination of the above. In some configurations, such as where portion(s) of device 102 are external to the patient, the electrode(s) coupling device 102 to heart 104 may include a skin surface electrode external to the patient. The electrodes may be associated with the heart for bipolar (i.e., two electrodes that are relatively close together) or for unipolar (i.e., two electrodes that are farther apart) signal sensing or therapy energy delivery (e.g., pacing pulse or shocks).

In the example of FIG. 1, device 102 includes a cardiac signal detector 110 having an input coupled to heart 104 by electrodes associated with heart 104 in a suitable manner for sensing an intrinsic cardiac signal. Detector 110 typically includes a sense amplifier for acquiring and amplifying the cardiac signal. Detector 110 may also include one or more continuous-time and/or discrete time (e.g., switched-capacitor) filter circuits, such as for selectively emphasizing the desired heart depolarization information relative to other acquired signal content. Detector 110 may also include an analog-to-digital converter (ADC) to convert continuous-time and/or discrete time samples into numerical representations of those samples. Detector 110 may also include one or more digital filters (or other digital signal processing circuitry) following the ADC, such as for selectively emphasizing the desired heart depolarization information relative to other acquired signal content.

Detector 110 also extracts heart depolarizations (or another feature corresponding to a heart contraction) from the sensed intrinsic cardiac signal associated with each electrode, together with the corresponding time of occurrence of the depolarization. In one example, detector 110 detects depolarizations using a level detector circuit. Detector 110 outputs an indication of the occurrence (and time) of the depolarization to controller 114 circuit for further processing. Controller 114 is capable of sequencing through various control states such as, for example, by using a digital microprocessor having executable instructions stored in an associated instruction memory circuit, a microsequencer, or a state machine. In operation, by executing these instructions, controller 114 provides control signals to cardiac signal detector 110 and an energy output circuit 118. In this example, controller 114 includes an arrhythmia detector module 122, for detecting an arrhythmia based on the depolarization information from cardiac signal detector 110 (e.g., detecting depolarizations above a critical rate may indicate a tachyarrhythmia). Controller 114 also includes an arrhythmia classifier 124, for classifying the detected arrhythmia, such as according to a sequence in which a heart contraction depolarization is received at various electrodes. Controller 114 also includes a therapy map 126 stored in memory, mapping a predetermined therapy (or list of therapies) to each arrhthmia classification. Among other things, the control signals from controller 114 to energy output circuit 118 direct the appropriate delivery of antitachyarrhythmia therapy based on the nature of the arrhythmia as sensed from the electrodes by cardiac signal detector 110 and as classified by controller 114. Energy output circuit 118 is coupled to one or more electrodes associated with the heart 104. Energy output circuit 118 provides pacing or resynchronization pulses, defibrillation shocks, or other appropriate cardiac therapy to heart 104. Device 102 also includes a battery or other power source 120.

Figure 2:
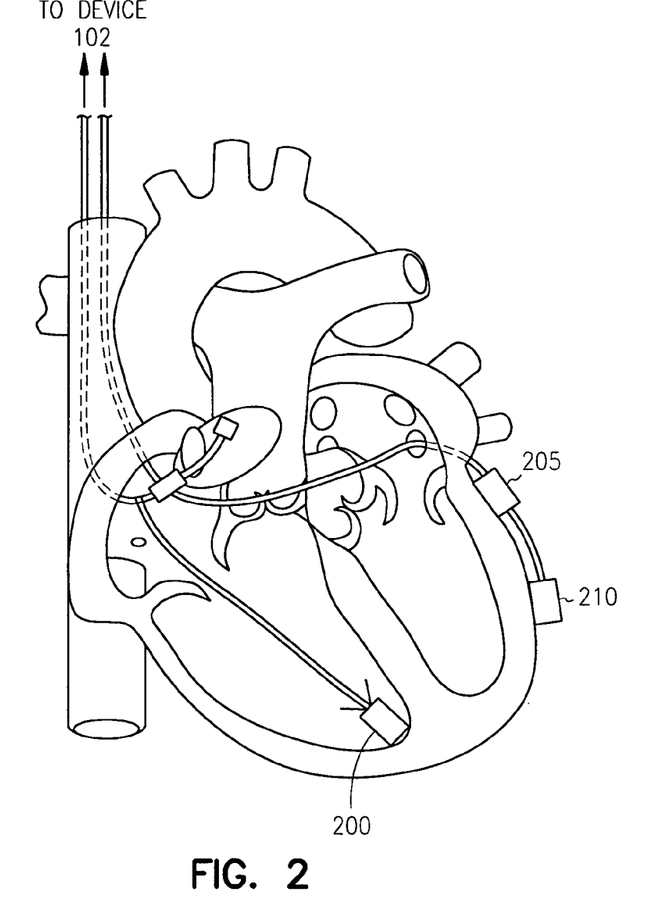
FIG. 2 is a schematic illustration of an example electrode configuration for one example classifying an arrhythmia and selecting appropriate electrode(s) and/or a therapy regimen to be delivered from the selected electrode(s).

FIG. 2 is a schematic illustration of an example electrode configuration for use with one example of the present technique for classifying an arrhythmia and selecting appropriate electrode(s) and/or a therapy regimen to be delivered from the selected electrode(s). In this example, device 102 is associated with heart 104 using an intravascular right ventricular (RV1) electrode 200, which is disposed at or near the apex of the right ventricle of heart 104. First and second left ventricular (LV1, LV2) electrodes 205 and 210, respectively, are introduced through a coronary sinus into the great cardiac vein into association with the left ventricle of heart 104. In this example, LV1 electrode 205 is located near a basal portion of the left ventricle, and LV2 electrode 210 is located near a more apical portion of the left ventricle. FIG. 2 is merely an illustrative example of one possible electrode configuration for use with the present system and methods, other suitable electrode configurations may include fewer electrodes or more electrodes, and may be disposed elsewhere in association with heart 104.

Figure 3:
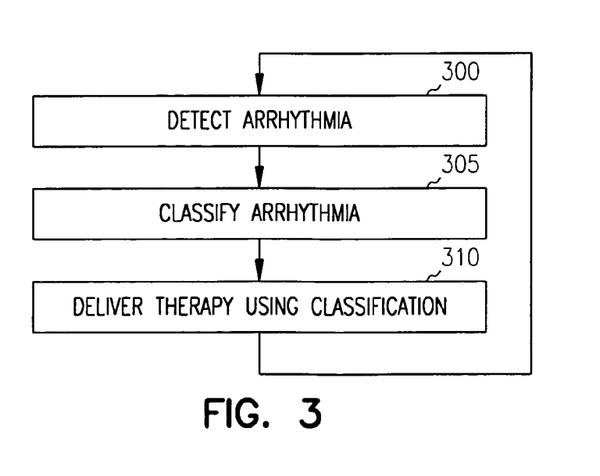
FIG. 3 is a flow chart illustrating generally an overview of one example of a method for classifying and treating an arrhythmia.

FIG. 3 is a flow chart illustrating generally an overview of one example of a method carried out by device 102 (e.g., by executing a sequence of instructions using controller 114) for classifying and treating an arrhythmia. At 300, an arrhythmia is detected. For example, the arrhythmia may be detected by detecting a rate of heart depolarizations associated with a particular chamber, and comparing the rate to one or more threshold values. For example, a detected depolarization rate exceeding a critical rate threshold value may be deemed a tachyarrhythmia. At 305, the arrhythmia is classified, for example, by noting the temporal order in which a depolarization associated with a particular heart contraction was received at multiple electrodes (e:g., RV then V1 then LV2, or LV1 then RV then LV2, etc.). At 310, a therapy is delivered based upon the classification such as, for example, by mapping a particular therapy to each arrhythmia classification. In a further example, the particular therapy that is delivered may depend on whether that therapy was previously successful at treating that arrhythmia.

TABLE 1

Example of Arrhythmia Classification and Therapy Selection.

| Detection Sequence | Arrhythmia Classification | Therapy |
|---|---|---|
| (RV1, LV1, LV2) | AR1 | TH1 |
| (RV1, LV2, LV1) | AR2 | TH2 |
| (LV1, RV1, LV2) | AR3 | TH3 |
| (LV1, LV2, RV1) | AR4 | TH4 |
| (LV2, RV1, LV1) | AR5 | TH5 |
| (LV2, LV1, RV1) | AR6 | TH6 |

Table 1 illustrates one possible arrhythmia classification scheme, with each classified arrhythmia mapped to at least one therapy. As discussed below, however, each therapy TH1, TH2, etc. may represent a single antiarrhythmia therapy, or may instead represent a ranked or other list of therapies, from which a particular therapy is selected. In this example, the arrhythmia is classified based on the order in which a depolarization (or other feature) associated with a particular heart contraction is received at the various electrodes illustrated in FIG. 2. For example, the sequence (RV1, LV1, LV2) represents an arrhythmia state for which a heart contraction is detected first at RV1 electrode 200, then at LV1 electrode 205, then at LV2 electrode 210.

This classification may be performed with respect to a single heart contraction during the arrhythmia. Alternatively, the classification is repeatedly performed over a plurality of heart contractions during the arrhythmia. In that case, the most prevalent sequence (if any) is used to classify the arrhythmia. Moreover, an indication of the prevalence and/or variability of the sequence may also be provided. In one example, such a prevalence indication is relevant to the "confidence" that the arrhythmia is properly classified. In another example, such a variability indication is relevant to whether the arrhythmia is stable or unstable. Therefore, this prevalence or variability indication may also be used as a factor for determining which therapy to invoke. For example, TH1 may be an antitachyarrhythmia pacing (ATP) sequence issued from a particular electrode or set of electrodes in a particular way, but if the arrhythmia classification variability indicator indicates that the arrhythmia is unstable, the mapped therapy TH1 may be overridden and a more painful (but likely more effective) countershock issued instead.

In a further example, the six arrhythmia classifications in Table 1 are expanded to 54 possible arrhythmia classifications by including information about the relative time difference with which the same heart contraction was detected at the different electrodes, and classifying that time difference, for example, into three possible states. By way of illustrative example, but not by way of limitation, a time difference that is less than or equal to 10 milliseconds is deemed small ("S"), a time difference that is between 10 milliseconds and 50 milliseconds is deemed medium ("M"), and a time difference that equals or exceeds 50 milliseconds is deemed large ("L"). Using these three categorizations of the timing relationships, each detection sequence entry in Table 1 can be expanded into nine timing sequence entries. An example of such an expansion of the first detection sequence entry in Table 1, (RV1, LV1, LV2), is illustrated below in Table 2.

TABLE 2

Example of expansion of (RV1, LV1, LV2) in Table 1

| Detection Sequence Timing | Arrhythmia Classification | Therapy |
|---|---|---|
| (RV1, S, LV1, S, LV2) | AR1 | TH1 |
| (RV1, S, LV1, M, LV2) | AR2 | TH2 |
| (RV1, M, LV1, S, LV2) | AR3 | TH3 |
| (RV1, M, LV1, M, LV2) | AR4 | TH4 |
| (RV1, S, LV1, L, LV2) | AR5 | TH5 |
| (RV1, L, LV1, S, LV2) | AR6 | TH6 |
| (RV1, L, LV1, L, LV2) | AR7 | TH7 |
| (RV1, M, LV1, L, LV2) | AR8 | TH8 |
| (RV1, L, LV1, M, LV2) | AR9 | TH9 |

In Table 2, for example, the third entry (RV1, M, LV1, S, LV2), represents a heart contraction that is detected first at RV1 electrode 200, followed by a detection of the same heart contraction at LV1 electrode 205 that occurs between 10 and 50 milliseconds after the detection at RV1 electrode 200, followed by a detection of the same heart contraction at LV2 electrode 210 that occurs less than or equal to 10 milliseconds after the detection at LV1 electrode 205. This detection timing sequence is mapped to a particular arrhythmia classification, AR3, which, in turn, is mapped to at least one therapy, TH3.

Tables similar to Table 2 can be created for each of the entries in Table 1, yielding, in this example, 54 arrhythmia classifications, each mapped to a corresponding therapy or therapies.

The arrhythmia classification techniques discussed in this document need not be performed using only temporal sequence and timing differences. Other physiological information can also be used perform the classification. For example, the detected heart rate may be compared to one or more user-programmable thresholds to determine a heart rate zone used to further classify the arrhythmia. One suitable example providing three rate zones (referred to as "VT-1," "VT," and "VF") for classifying arrhythmias is described in Krig et al. U.S. Pat. No. 5,978,707, entitled APPARATUS AND METHOD FOR TREATING VENTRICULAR ARRHYTHMIAS, which is assigned to Cardiac Pacemakers, Inc., and which is incorporated herein by reference in its entirety, including its disclosure of classifying arrhythmias according to heart rate zones, and of providing antiarrhythmia therapy based on the heart rate zone classification, and of providing various ATP and other antiarrhythmia therapy schemes. One suitable example of displaying such rate zone and other parameter information for the user is described in Conley et al. U.S. Pat. No. 6,289,248, entitled APPARATUS AND METHOD FOR TREATING VENTRICULAR ARRHYTHMIAS, which is assigned to Cardiac Pacemakers, Inc., and which is incorporated herein by reference in its entirety, including its disclosure of displaying, on an external interface device, parameters for classifying arrhythmias according to heart rate zones, and of displaying parameters for providing antiarrhythmia therapy based on the heart rate zone classification. An example of expanding the first detection sequence entry in Table 1, (RV1, LV1, LV2), to also use a heart rate zone arrhythmia classification, such as discussed in Krig et al. U.S. Pat. No. 5,978,707, is illustrated below in Table 3.

TABLE 3

Example of expansion of (RV1, LV1, LV2) in Table 1.

| Detection Sequence and Heart Rate Zone | Arrhythmia Classification | Therapy |
| --- | --- | --- |
| (RV1, LV1, LV2, VT-1) | AR1 | TH1 |
| (RV1, LV1, LV2, VT) | AR2 | TH2 |
| (RV1, LV1, LV2, VF) | AR3 | TH3 |

Figure 4:
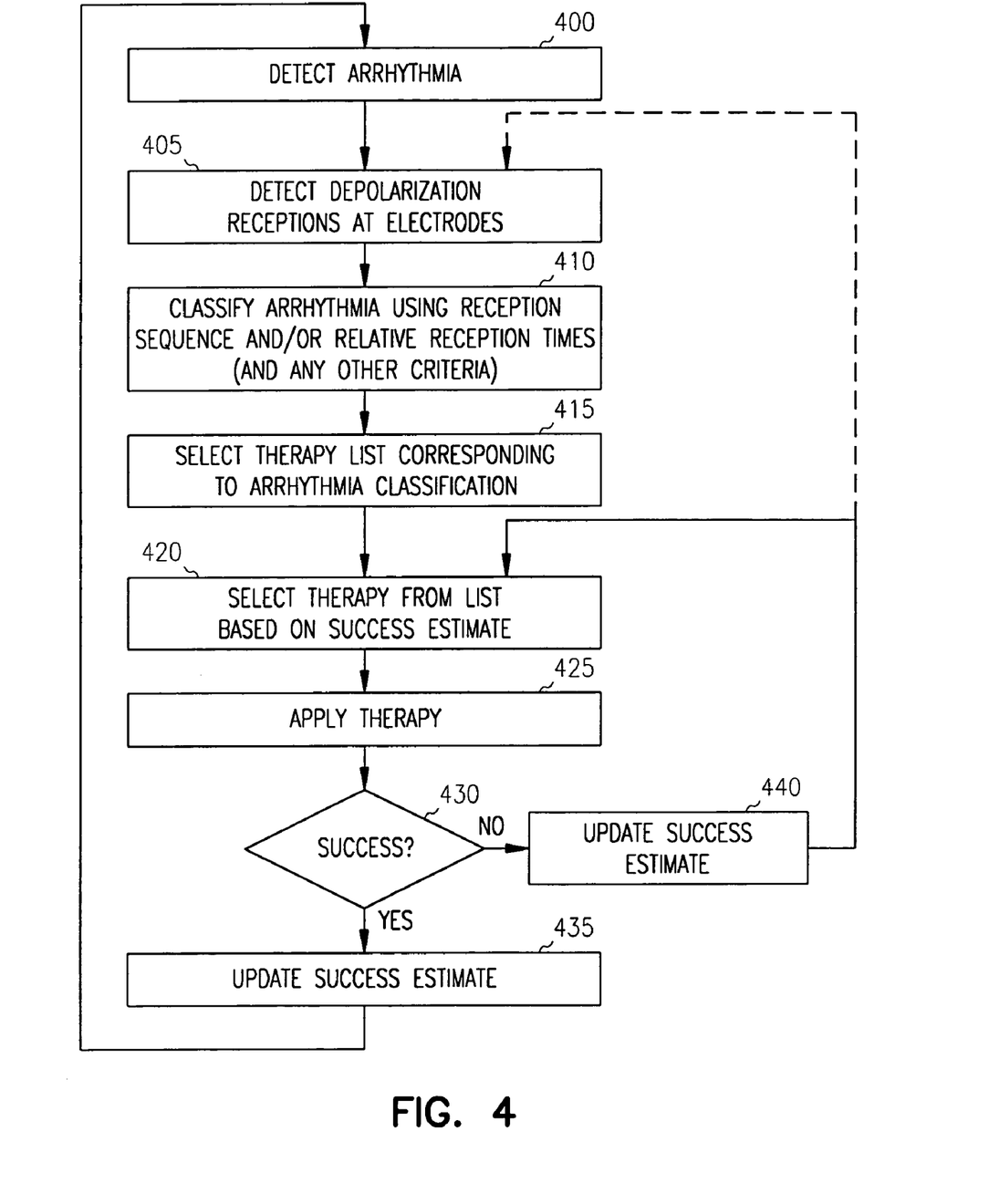
FIG. 4 is a flow chart illustrating generally another example of a method for classifying and treating an arrhythmia.

FIG. 4 is a flow chart illustrating generally another example of a method carried out by device 102 for classifying and treating an arrhythmia. At 400, an arrhythmia is detected, for example, by detecting a rate of heart depolarizations associated with a particular chamber, and comparing the rate to one or more threshold values (e.g., rate exceeding a critical rate threshold value may be deemed a tachyarrhythmia). At 405, the relative sequence in which a particular depolarization or other indication of a particular heart contraction is received at the electrodes is detected. This may further include computing and/or classifying the relative time differences between the detections at the various electrodes. At 410, the arrhythmia is classified, for example, by noting the temporal order (i.e., relative sequence) in which a depolarization associated with a particular heart contraction was received at multiple electrodes (e.g., RV then LV1 then LV2, or LV1 then RV then LV2, etc.). As illustrated in Table 2, the classification may further use the time differences between the receptions of the depolarization and the various electrodes. As illustrated in Table 3, the classification may further use a heart rate zone, or other physiological information. At 415, based on the arrhythmia classification, a therapy is selected from a corresponding therapy list that is mapped to that arrhythmia classification. While each therapy list may include a single therapy, in one example, the therapy list includes a plurality of therapies, each therapy having a corresponding probability or other estimate of its successfulness in treating the classified arrhythmia. At 420, a particular therapy from the therapy list corresponding to the arrhythmia classification is selected using the success estimates for the therapies on the therapy list. For example, a therapy having an associated high success estimate (e.g., based on a previous successful treatment of the classified arrhythmia using the therapy), is more likely to be selected than a therapy having an associated lower success estimate. The success estimate may also factor in any undesirability of applying the therapy to the patient such as, for example, the pain experienced when a defibrillation countershock is delivered to the patient. At 425, the therapy is applied to the heart, such as via the electrodes associated with the heart. At 430, a determination is made as to whether the application of the therapy succeeded at treating the arrhythmia. For example, a decrease in heart rate below a critical threshold value may indicate successful treatment of a tachyarrhythmia. If, at 430, the therapy was successful at treating the arrhythmia, then at 435, the success estimate of the applied therapy is updated to reflect this success, and process flow returns to 400 to await detection of another arrhythmia. If, at 430, the therapy was not successful at treating the arrhythmia, then at 440 the success estimate of the applied therapy is updated to reflect this failure, and process flow returns to 420 to select another therapy from the therapy list associated with the classified arrhythmia.

Figure 5:
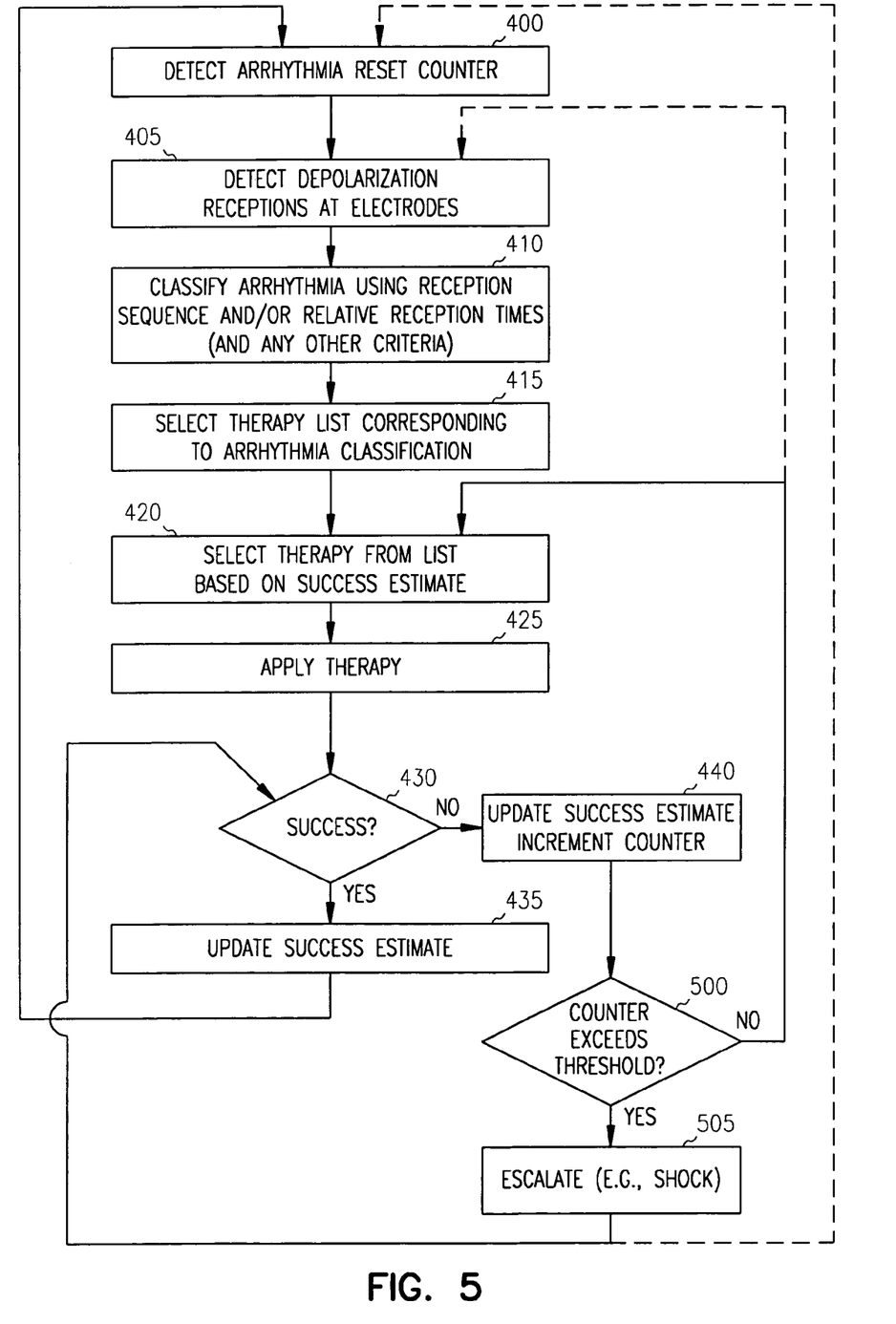
FIG. 5 is a flow chart illustrating generally another example of a method for classifying and treating an arrhythmia.

In a further example, a predetermined number of failures at 430 triggers an escalated therapy (e.g., defibrillation shock) believed more effective at treating the arrhythmia, but which has been withheld because of other undesirable effects such as, for example, the pain experienced by a patient upon receiving a defibrillation shock, and unnecessary battery depletion and shortened device longevity from delivering the shock. An example of this technique is illustrated in the flow chart FIG. 5, which is slightly modified from that of FIG. 4. In FIG. 5, at 400, upon detection of the arrhythmia, a counter is also reset. After therapy is applied at 425, if the therapy was not successful in interrupting the tachyarrhythmia, as determined at 430 (e.g., by redetecting whether an arrhythmia is still present), then the success estimate is updated at 440, and the counter is incremented. Then, at 500 if the counter exceeds a predetermined threshold (e.g., three failures), therapy is escalated by delivering a shock at 505. Process flow returns to 430 to determine whether the delivered shock was successful. If, at 500, the counter does not exceed the predetermined threshold, another therapy is selected from the therapy list corresponding to the classified tachyarrhythmia.

In FIGS. 4 and 5, an unsuccessful application of antiarrhythmia therapy at 425 may, however, effectively change the nature of the arrhythmia such that it would be differently classified at 410 and, therefore, perhaps differently treated. Accordingly, in an alternative method of operation, process flow from 440 and 500 returns to 405, rather than to 420, as illustrated by the extended dashed lines in FIGS. 4 and 5. Similarly, process flow from 505 returns to 400, rather than to 430, as illustrated by the extended dashed line in FIG. 5. Such techniques allows the arrhythmia to be reclassified at 410 to determine whether the previously-applied therapy effectively changed the earlier arrhythmia classification.

In FIGS. 4 and 5, the success estimate may initially be seeded (e.g., at the factory or via programming by a physician or other user) to reflect an initial estimate of how successful a particular therapy in the therapy list will be at treating the particularly classified arrhythmia. If the user has no inclinations toward a particular therapy, for example, each therapy on the list could be seeded with a 50% success estimate, with the success estimate updated according to the number of successes for that therapy divided by the total number of trials of that therapy. Otherwise, FIGS. 4 and 5 reflect a continuous looping process, such that the illustrated acts are invoked whenever an arrhythmia is detected at 400 in a patient.

Figure 6:
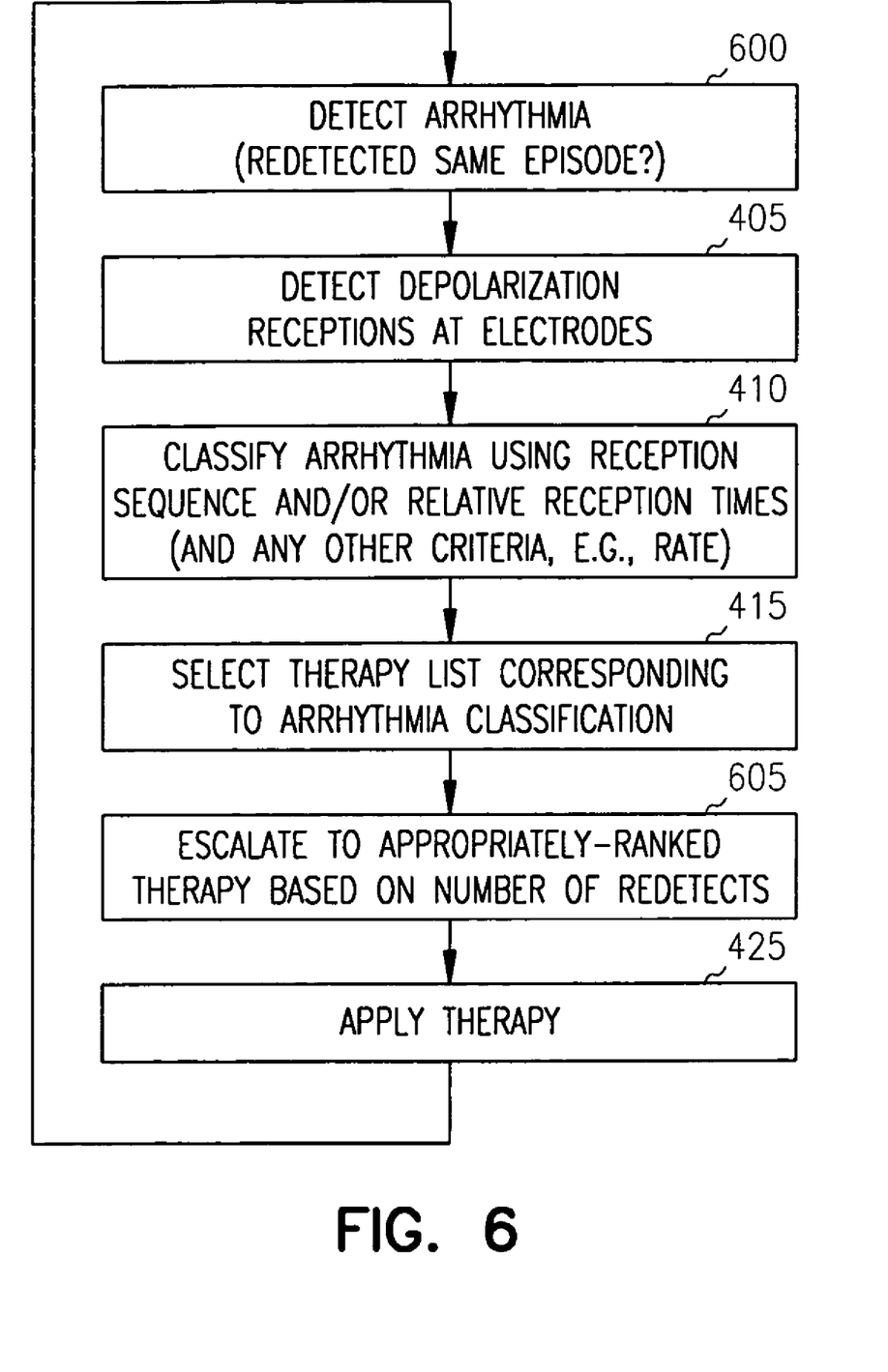
FIG. 6 is a flow chart illustrating an example of classifying an arrhythmia and escalating to an appropriately-ranked therapy, such using a number of times an arrhythmia has been redetected during a particular arrhythmia episode.

FIG. 6 is a flow chart illustrating an alternate example of classifying an arrhythmia and escalating to an appropriately-ranked therapy within a list corresponding to the arrhythmia classification, such as based on a number of times an arrhythmia has been redetected during a particular arrhythmia episode. At 600, an arrhythmia is detected, such as using the techniques discussed above. By comparing a timer value (which was started upon a previous arrhythmia detection) to a predetermined threshold value, the arrhythmia is deemed to be a redetected occurrence of the same arrhythmic episode if the timer value is less than the predetermined comparison value. At 405, depolarization receptions are detected at electrodes, such as using the techniques discussed above. At 410, the arrhythmia is classified using a depolarization reception sequence and/or relative depolarization reception times, together with any other suitable criteria for classifying an arrhythmia (e.g., heart rate within a particular heart rate zone, as discussed above). At 415, a therapy list, corresponding to the arrhythmia classification, is selected. The therapy list includes a predetermined number (e.g., five) of ranked therapies, some or all of which may be user-programmable. At 605, a particular therapy in the selected therapy list is selected based on the number of times the arrhythmia has been redetected during the same arrhythmic episode (however, the arrhythmia may alternatively represent a new arrhythmic episode). For example, a newly detected arrhythmia episode may be given an index of "0" within the therapy list. This would correspond to a less severe therapy than an arrhythmia that has been redetected twice, which may be given an index of "2" within the therapy list, corresponding to a more severe therapy. At 425 the selected therapy is delivered, as discussed above. In one implementation of this technique, the arrhythmia may be reclassified during the same arrhythmic episode, but the ranking in the new therapy list is based on a number of arrhythmia redetections after therapy is applied from any of the therapy lists. In another implementation of this technique, if the arrhythmia is reclassified during the same arrhythmic episode, the ranking in the new therapy list is based on a number of arrhythmia redetections after therapy was applied from that particular new therapy list.

In the example of FIG. 6, if the arrhythmic episode should persist even after the highest-ranked (most severe) therapy is delivered, in one example, antiarrhythmia therapy is subsequently inhibited during the remainder of that arrhythmia episode. In another example, such a persistent arrhythmic episode continues to trigger therapy delivery. In a further example, whether such a persistent arrhythmic episode continues to deliver therapy depends at least in part on the arrhythmia classification.

In Tables 1 and 2 above, each therapy TH1, TH2, etc. may represent a single therapy that is mapped to the corresponding arrhythmia, or instead, each may represent a plurality of ranked or unranked therapies, each of which is mapped to the corresponding arrhythmia. For example, TH1 may include several possible antitachyarrhythmia pacing (ATP) therapies, several possible cardioversion therapies, and several possible shock therapies. An ATP therapy typically provides one or more pacing pulses timed to interrupt a reentrant loop heart depolarization (e.g., due to scar tissue) causing the tachyarrhythmia. This can be accomplished with a single pulse or a series of pulses, one of which is timed correctly to enter the reentrant loop termination zone. ATP therapy may involve several parameters; different combinations of parameter settings may be regarded as distinct therapies on the therapy list TH1, TH2, etc. Such ATP parameters may include, among other things, number of pulses, timing of the first pulse with respect to an immediately preceding sensed ventricular depolarization (referred to as a coupling interval), timing between ATP pulses (each ATP pulse corresponding to a particular heart contraction) in an ATP sequence of ATP pulses, and interelectrode timing for a particular ATP pulse. Other ATP parameters control various schemes for overdriving the intrinsic heart rate with an ATP sequence, then ramping down the ATP pulse delivery rate, suddenly lowering the ATP pulse delivery rate, or stopping abruptly the delivery of ATP pulses altogether at the end of the ATP sequence. One example of delivering one or more ATP pulses is discussed in Spinelli et al. U.S. Pat. No. 6,885,890, entitled "APPARATUS AND METHOD FOR MULTI-SITE ANTI-TACHYCARDIA PACING," which is assigned to Cardiac Pacemakers, Inc., and which is incorporated herein by reference in its entirety.

A particular therapy may differ from other therapies by, among other things, being delivered from one or more different electrodes. For example, for the electrode configuration illustrated in FIG. 2, ATP can be delivered from the following electrode(s): (RV), (LV1), (LV2), (RV, LV1), (RV, LV2), (LV1, LV2), (RV, LV1, LV2). Each such electrode combination may represent a distinct therapy on a list of therapies such as TH1.

Moreover, where an ATP pulse or sequence of pulses is delivered from more than one electrode, the ATP pulses can be delivered simultaneously from the electrodes, or may incorporate a slight temporal offset from the delivery of a corresponding pulse to one or more other electrodes. For example, for the electrode configuration illustrated in FIG. 2, ATP can be delivered using the following electrode sequences: (RV), (LV1), (LV2), (RV, LV1), (LV1, RV), (RV, LV2), (LV2, RV), (LV1, LV2), (LV2, LV1), (RV, LV1, LV2), (RV, LV2, LV1), (LV1, RV, LV2), (LV1, RV, LV2), (LV1, LV2, RV), (LV2, RV, LV1), (LV2, LV1, RV). Each such electrode sequence may constitute a distinct therapy on a list of therapies such as TH1.

Moreover, an ATP pulse sequence can trigger a particular heart contraction by issuing these pulses either simultaneously, or using predetermined temporal offset value(s) to resynchronize or otherwise better coordinate the spatial nature of the heart depolarization wave associated with the heart contraction. Therefore, each of the above therapies can be further expanded into a list of therapies that incorporates such temporal offset information. In one example, this relative interelectrode timing is classified as follows: "S," indicating simultaneous pulse issuance at two electrodes, "SM" indicating that a pulse is delivered from the second electrode in the sequence at a small (e.g., less than or equal to 10 millisecond) predetermined delay from the first electrode in the sequence, "M" indicating that the pulse is delivered from the second electrode in the sequence at a medium (e.g., between 10 and 20 millisecond) predetermined delay from the first electrode in the sequence, and "H," indicating that the pulse is delivered from the second electrode in the sequence at a high (e.g., greater than or equal to 20 millisecond) predetermined delay from the first electrode in the sequence. For an illustrative example, the sequence (RV, LV1) above can be thus expanded as the following therapies: (RV, S, LV1), (RV, SM, LV1), (RV, M, LV1), and (RV, H, LV1). The therapy list corresponding to a particular arrhythmia, however, need not include the complete expanded list of therapies. A predetermined subset of available therapies may be factory-set or programmably selected by a physician or other user, as being mapped to a particular arrhythmia.

Among other things, the present inventors have recognized that the detection sequence and/or detection sequence timing of a particular arrhythmia may suggest or even determine the most appropriate sequence in which ATP pulses should be delivered to treat that particular arrhythmia. For an illustrative example, a (RV1, M, LV1, M, LV2) arrhythmia detection sequence may suggest delivering an ATP therapy using a (RV, M, LV1, M, LV2) temporal offset arrangement for an ATP pulse in an ATP pulse sequence. In another example, a (RV1, S, LV1, M, LV2) arrhythmia detection sequence may suggest delivering an ATP therapy using a (RV1, S, LV1, M, LV2) temporal offset arrangement for an ATP pulse in a ATP pulse sequence.

Figure 7:
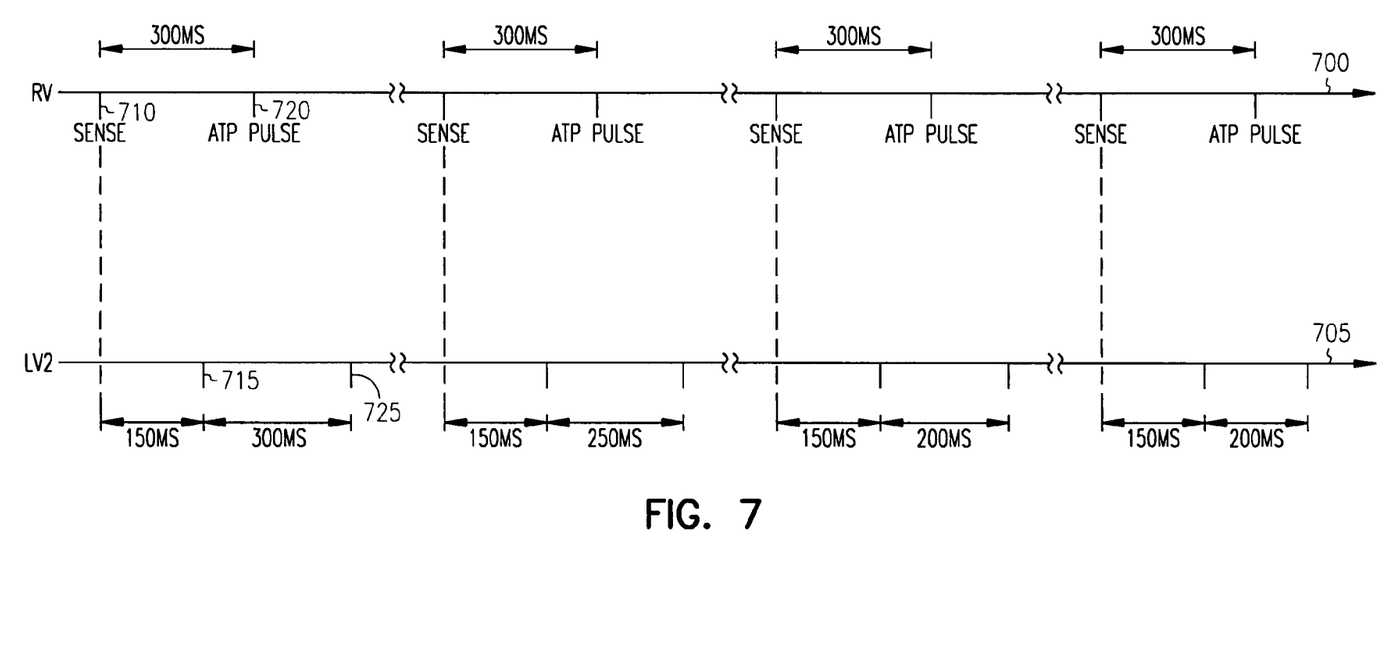
FIG. 7 is a timing diagram for two electrodes, in which an interelectrode delay is decreased to maintain a substantially constant coupling interval.

The interelectrode temporal offset intervals for a particular ATP pace pulse need not be fixed. In one example, a sequence of ATP pace pulses is delivered at a constant coupling interval while sequentially ramping down (decreasing) the interelectrode delay. One example of such an ATP therapy is illustrated in the timing diagram of FIG. 7, which uses a two electrode configuration (e.g., RV and LV2 of FIG. 2) as an illustrative example. In FIG. 7, trace 700 represents timing of signals occurring at RV electrode 200. Trace 705 represents timing of signals occurring at LV2 electrode 210. At 710, a ventricular depolarization is sensed at RV electrode 200, triggering delivery of an ATP pace pulse at 720. At 715, the same ventricular depolarization is sensed at LV2 electrode 210, triggering delivery of an ATP pace pulse at 725. In this illustration, the coupling interval is defined as the time between the earliest sense of a particular ventricular depolarization at one of the electrodes associated with the ventricles and the immediately succeeding delivery of an ATP pulse at that same electrode. In FIG. 7, for example, the coupling interval is the time between 720 and 710. In one example, the interelectrode delay between delivering ATP pulses (e.g., the time between 725 and 720) is incrementally or otherwise decreased during successive ATP pulses in the ATP sequence. For example, in FIG. 7, where the coupling interval is 300 milliseconds, and the interelectrode sensing delay (e.g., the time between 715 and 710) is 150 milliseconds, the first ATP pulse in the ATP pulse sequence is delivered from each electrode at 300 milliseconds after its respective sense. Then, the interelectrode pacing delay is incrementally decreased to 100 milliseconds, then 50 milliseconds, then 0 milliseconds on subsequent ATP pulses, as illustrated in FIG. 7. Thus, FIG. 7 illustrates one example of a particular ATP therapy sequence constituting one therapy on a list of therapies mapped to a particular classified arrhythmia.

In addition to the distinct ATP therapies discussed above, a cardioversion or defibrillation shock therapy may also be expanded into a plurality of possible therapies that may be included on a particular therapy list such as TH1. For example, a defibrillation shock may be provided using several different energy levels and/or waveforms each of which may constitute a distinct therapy on a particular therapy list such as TH1. Examples of variations in antitachyarrhythmia therapy, including discrete ATP therapies and discrete defibrillation shock therapies, are discussed in Krig et al. U.S. Pat. No. 6,151,524, entitled "APPARATUS AND METHOD FOR TREATING VENTRICULAR TACHYARRHYTHMIAS," which is assigned to Cardiac Pacemakers, Inc., and which is incorporated herein by reference in its entirety. This patent also describes techniques for escalating to a second therapy if a first therapy fails to interrupt the tachyarrhythmia.

CONCLUSION

It is to be understood that the above description is intended to be illustrative, and not restrictive. For example, the above-discussed embodiments may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein."

What is claimed is:

1. An implantable cardiac rhythm management device for coupling to a plurality of electrodes for association with a heart, the device including:
   a cardiac signal detector circuit, for coupling to the electrodes;
   an energy output circuit, coupled to at least one of the electrodes; and
   a controller, coupled to the cardiac signal detector and the energy output circuit, the controller including:
      an arrhythmia detector module, to detect an arrhythmia;
      an arrhythmia classifier module, to classify the detected arrhythmia into an arrhythmia classification that specifies: (a) a sequence in which a same heart contraction depolarization is received by at least three of the electrodes, wherein at least two electrodes are associated with different heart chambers, and (b) values of relative interelectrode time that the same heart contraction depolarization is received by the three electrodes;
      a therapy map, providing an antiarrhythmia therapy corresponding to the arrhythmia classification, wherein an antiarrhythmia therapy is delivered according to an electrode sequence that is mapped to the relative interelectrode time; and
      a control signal to be issued to the energy output circuit for delivering a selected antiarrhythmia therapy corresponding to an arrhythmia classification.

2. The device of claim 1, in which the arrhythmia classifier module classifies the detected arrhythmia into an arrhythmia classification that specifies: (a) a sequence in which the heart contraction depolarization is received by a plurality of electrodes that are associated with different heart chambers and with the same heart chamber, and (b) values of relative interelectrode time at which the heart contraction depolarization is received by the electrodes that are associated with different heart chambers and with the same heart chamber.

3. The device of claim 1, in which the controller permits selecting the antiarrhythmia therapy corresponding to the arrhythmia classification, including selecting the antiarrhythmia therapy from a list of antiarrhythmia therapies that are mapped to the arrhythmia classification.

4. The device of claim 3, in which the controller permits selecting the antiarrhythmia therapy from the list based on a corresponding success estimate obtained from historical data about how successful a particular antiarrhythmia therapy has previously been in treating similarly classified arrhythmias.

5. The device of claim 4, in which the controller permits updating the success estimate after issuing the control signal and determining whether the delivered therapy was successful at treating the arrhythmia.

6. The device of claim 5, in which the controller permits escalating to a different antiarrhythmia therapy if the delivered therapy was unsuccessful at treating the arrhythmia.

7. The device of claim 4, in which the controller permits selecting the antiarrhythmia therapy from the list at least in part by factoring in an undesirability of a side effect of applying the antiarrhythmia therapy.

8. The device of claim 3, in which the controller permits selecting the antiarrhythmia therapy from the list at least in part by factoring in an undesirability of a side effect of applying the antiarrhythmia therapy.

9. The device of claim 1, in which the arrhythmia detector permits determining whether the delivered antiarrhythmia therapy is successful at treating the arrhythmia.

10. The device of claim 9, in which the controller permits updating the success estimate based on whether the delivered antiarrhythmia therapy was successful at treating the arrhythmia.

11. The device of claim 1, in which the arrhythmia detector permits determining whether the delivered antiarrhythmia therapy is successful at treating the arrhythmia, and the controller escalates to a higher-confidence antiarrhythmia therapy after a specified number of failures in treating the detected arrhythmia.

12. The device of claim 1, in which the arrhythmia classifier module is configured to again classify the detected arrhythmia after an antiarrhythmia therapy is delivered without successfully treating the arrhythmia.

13. A machine-assisted method including:
    detecting an arrhythmia at a plurality of electrodes;
    classifying a detected arrhythmia into an arrhythmia classification that specifies (a) a sequence in which a same heart contraction depolarization is received by at least three of the electrodes, wherein at least two electrodes are associated with different heart chambers, and (b) values of relative interelectrode time that the same heart contraction depolarization is received by the three electrodes;
    selecting an antiarrhythmia therapy corresponding to an arrhythmia classification of the detected arrhythmia, wherein an antiarrhythmia therapy is delivered according to an electrode sequence determined using the relative electrode time; and
    delivering a selected antiarrhythmia therapy by issuing a control signal to the energy output circuit.

14. The method of claim 13, in which the classifying comprises obtaining a classification specifying (a) a sequence in which the heart contraction depolarization is received by a plurality of electrodes that are associated with different heart chambers and with the same heart chamber, and (b) values of interelectrode time at which the heart contraction depolarization is received by the electrodes that are associated with different heart chambers and with the same heart chamber.

15. The method of claim 13, in which the selecting the antiarrhythmia therapy includes selecting the antiarrhythmia therapy using a corresponding success estimate obtained from historical data about how successful a particular antiarrhythmia therapy has previously been in treating similarly classified arrhythmias.

16. The method of claim 15, including updating the success estimate after issuing the control signal and determining whether the delivered therapy was successful at treating the arrhythmia.

17. The method of claim 16, including escalating to a different antiarrhythmia therapy if the delivered therapy was unsuccessful at treating the arrhythmia.

18. The method of claim 15, including updating the success estimate according to whether the delivered antiarrhythmia therapy successfully treated the arrhythmia.

19. The method of claim 13, in which the selecting the antiarrhythmia therapy includes factoring in an undesirability of a side effect of applying the antiarrhythmia therapy.

20. The method of claim 13, including determining whether the delivered antiarrhythmia therapy is successful at treating the arrhythmia.

21. The method of claim 13, including:
    determining whether the delivered antiarrhythmia therapy was successful at treating the arrhythmia; and
    escalating to a higher-confidence antiarrhythmia therapy after a specified number of failures in treating the detected arrhythmia.

22. The method of claim 13, including:
    determining whether the delivered antiarrhythmia therapy was successful at treating the arrhythmia; and
    again classifying the detected arrhythmia if the antiarrhythmia therapy was delivered without successfully treating the arrhythmia.

23. A machine-assisted method including:
    detecting an arrhythmia at a plurality of electrodes;
    classifying a detected arrhythmia into an arrhythmia classification that specifies first information that is indicative of a sequence in which a same heart contraction is received by at least three of the electrodes and second information that includes values of relative interelectrode time that a same heart contraction depolarization is received by the three electrodes;
    selecting an antiarrhythmia therapy corresponding to an arrhythmia classification of the detected arrhythmia, the selecting including using a map listing a plurality of the arrhythmia classifications and respectively corresponding antiarrhythmia therapies, wherein an antiarrhythmia therapy is delivered according to an electrode sequence that is mapped to the values of relative interelectrode time; and
    delivering a selected antiarrhythmia therapy by issuing a control signal to the energy output circuit.

24. The method of claim 23, wherein classifying a detected arrhythmia includes a classification that specifies third information, in which the third information includes information about a sequence in which the heart contraction depolarization is received by at least two of the electrodes.

25. The method of claim 24, in which the third information includes information about the sequence in which the heart contraction depolarization is received by at least two of the electrodes that are associated with the same heart chamber.

26. The method of claim 24, in which the second information includes a value of a difference between the times at which the heart contraction depolarization is received by the at least two electrodes.

27. The method of claim 23, in which the selecting the antiarrhythmia therapy includes selecting the antiarrhythmia therapy using a corresponding success estimate obtained from historical data about how successful a particular antiarrhythmia therapy has previously been in treating similarly classified arrhythmias.

28. The method of claim 23, including:
    determining whether the delivered antiarrhythmia therapy was successful at treating the arrhythmia; and
    again classifying the detected arrhythmia if the antiarrhythmia therapy was delivered without successfully treating the arrhythmia.

* * * * *

UNITED STATES PATENT AND TRADEMARK OFFICE
CERTIFICATE OF CORRECTION

PATENT NO. : 7,664,549 B2
APPLICATION NO. : 11/125501
DATED : February 16, 2010
INVENTOR(S) : Spinelli et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1175 days.

Signed and Sealed this

Twenty-eighth Day of December, 2010

David J. Kappos
*Director of the United States Patent and Trademark Office*